(12) United States Patent
Kim et al.

(10) Patent No.: US 7,804,591 B2
(45) Date of Patent: Sep. 28, 2010

(54) WAFER INSPECTING METHOD

(75) Inventors: Ji-Hye Kim, Anyang-si (KR); Yu-Sin Yang, Seoul (KR); Jong-An Kim, Seoul (KR); Moon-Shik Kang, Yongin-si (KR); Ji-Young Shin, Seoul (KR)

(73) Assignee: Samsung Electronics Co., Ltd, Suwon-Si (KR)

( * ) Notice: Subject to any disclaimer, the term of this patent is extended or adjusted under 35 U.S.C. 154(b) by 761 days.

(21) Appl. No.: 11/693,356

(22) Filed: Mar. 29, 2007

(65) Prior Publication Data
US 2008/0049219 A1 Feb. 28, 2008

(30) Foreign Application Priority Data
Aug. 25, 2006 (KR) ...................... 10-2006-0081025

(51) Int. Cl.
*G01N 21/00* (2006.01)
(52) U.S. Cl. ................................... 356/237.4
(58) Field of Classification Search ........................ None
See application file for complete search history.

(56) References Cited
U.S. PATENT DOCUMENTS

| | | | |
|---|---|---|---|
| 5,640,200 A * | 6/1997 | Michael | 382/144 |
| 5,798,830 A * | 8/1998 | Srinivasan | 356/237.2 |
| 6,020,957 A * | 2/2000 | Rosengaus et al. | 356/237.4 |
| 6,122,397 A * | 9/2000 | Lee et al. | 382/149 |
| 6,169,282 B1 * | 1/2001 | Maeda et al. | 382/149 |
| 6,347,150 B1 * | 2/2002 | Hiroi et al. | 382/149 |
| 7,035,447 B2 | 4/2006 | Take | |
| 7,116,816 B2 * | 10/2006 | Tanaka et al. | 382/149 |
| 7,231,079 B2 * | 6/2007 | Okuda et al. | 382/145 |
| 7,388,979 B2 * | 6/2008 | Sakai et al. | 356/237.4 |

FOREIGN PATENT DOCUMENTS

| | | |
|---|---|---|
| KR | 10-0268147 | 7/2000 |
| KR | 1020010027367 A | 4/2001 |
| KR | 1020060008609 A | 1/2006 |

* cited by examiner

*Primary Examiner*—Gregory J Toatley, Jr.
*Assistant Examiner*—Juan D Valentin (57) ABSTRACT

A wafer inspecting method including the steps of: multi-scanning a pattern image of a unit inspection region in a normal state and a pattern image of a unit inspection region to be inspected, respectively, using different inspection conditions; comparing the multi-scanned pattern images in the normal state with the multi-scanned pattern images to be inspected obtained by the same inspection conditions, and storing differences between the pattern images as difference images; generating a discrimination difference image by calculating a balance between the stored difference images; and discriminating a defect from noise by using the discrimination difference image.

12 Claims, 5 Drawing Sheets

FIG. 1

| DETECTING IMAGE | REFERENCE IMAGE | DIFFERENCE IMAGE |
|---|---|---|
|  |  |  |

| | DIFFERENCE IMAGE OF FIRST MODE | DIFFERENCE IMAGE OF SECOND MODE | DIFFERENCE IMAGE OF FIRST MODE − DIFFERENCE IMAGE OF SECOND MODE |
|---|---|---|---|
| CONCERNED DEFECT |  |  |  |
| GRAY LEVEL SIGNAL VALUE | 150 | 50 | 100 |
| NOISE |  |  |  |
| GRAY LEVEL SIGNAL VALUE | 150 | 120 | 30 |

WAFER INSPECTING METHOD

CROSS-REFERENCE TO RELATED APPLICATION

This application claims priority from Korean Patent Application No. 2006-81025, filed Aug. 25, 2006, the disclosure of which is hereby incorporated herein by reference in its entirety.

BACKGROUND OF INVENTION

1. Technical Field

The present disclosure relates to a wafer inspecting method and, more particularly, to a wafer inspecting method that is used for inspecting a defect of a wafer.

2. Discussion of Related Art

Yield improvement is very critical in a semiconductor device fabricating process. In this regard, many different methods for achieving yield improvement have been suggested and carried out.

For example, a wafer inspection process is performed whenever each unit process for fabricating the semiconductor device is completed.

A wafer inspection process that inspects the exterior of a wafer is performed to determine whether to proceed with the next process, by checking the state of the wafer upon completing each unit process. The wafer inspection process is performed by using a wafer inspecting apparatus, such as a microscope.

Figure 1:
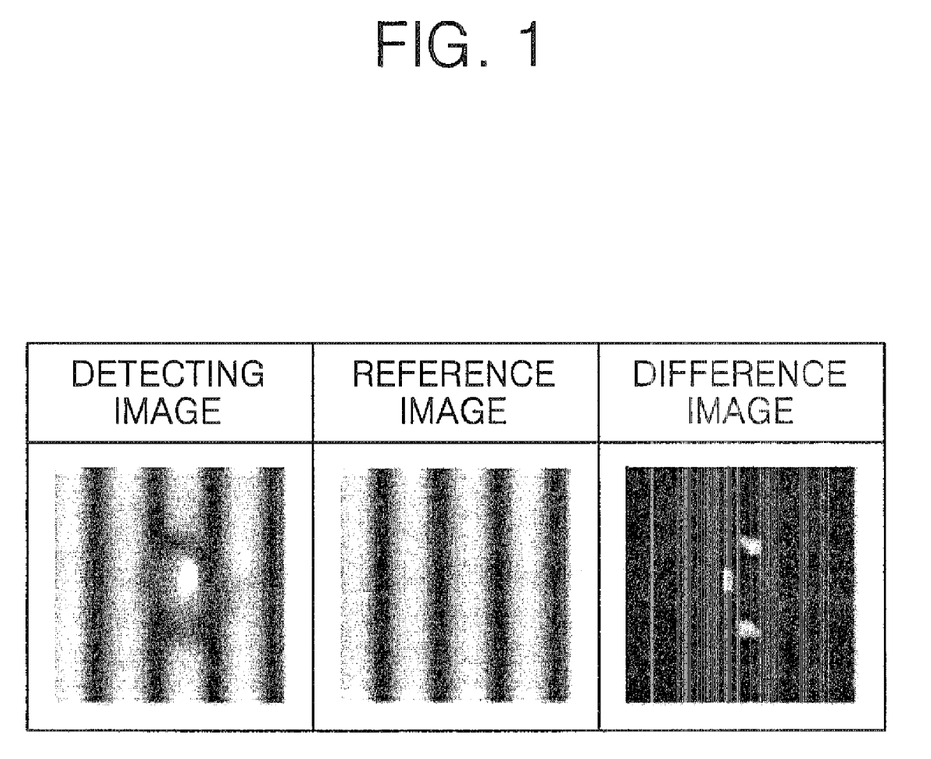
FIG. 1 provides images useful in explaining a conventional wafer inspecting method.

FIG. 1 is a view useful in explaining a conventional wafer inspecting method.

As illustrated in FIG. 1, the conventional wafer inspecting method is performed by first predetermining a unit inspection region, such as a cell or a die, and then comparing a scanned image of a pattern image in a normal state of the predetermined unit inspection region, hereinafter referred to as a "reference image", with a scanned image of a pattern image to be inspected in the predetermined unit inspection region hereinafter referred to as a "detection image".

When the reference image is different from the detection image, a difference of the images, that is, a difference image, is detected as a defect, as illustrated in FIG. 1.

In the conventional wafer inspecting method, however, noise including a pattern discoloration or a pattern brilliance, which do not affect the yield of a semiconductor device are detected as a defect of a wafer. More specifically, when a multilayer device such as a metal layer is inspected using the conventional method, not only a defect to be detected but also noise, such as pattern brilliance or grain reflecting light by crystals generated from metal particles, are detected as defects.

Consequently, since the conventional wafer inspecting method also detects noise when a defect of a wafer is detected, it is impossible to determine which portion of the wafer is weak and causes the defect, from a may displaying detected result.

SUMMARY OF THE INVENTION

Therefore, exemplary embodiments of the present invention are directed to provide a wafer inspecting method that easily discriminates an actual defect from noise when inspecting a wafer.

An exemplary embodiment of the present invention provides a wafer inspecting method that easily detects a defect when inspecting a wafer.

In accordance with an exemplary embodiment, the present invention provides a wafer inspecting method comprising: multi-scanning a pattern image of a unit inspection region in a normal state and a pattern image of a unit inspection region to be inspected with different inspection conditions; comparing the multi-scanned pattern images in the normal state with the multi-scanned pattern images to be inspected, by each of the same inspection conditions, and storing differences of the images as difference images; generating a discrimination difference image by calculating a balance between the stored difference images; and discriminating a defect from noise by using the discrimination difference image.

In an exemplary embodiment, the discriminating of a defect from noise may comprise calculating electrical signal values of the discrimination difference image and of the calculated signal values, and discriminating the signal values that exceed a predetermined threshold value as a defect and the signal values that are less than the threshold value as noise. In this exemplary embodiment, the electrical signal values may be gray level signal values.

In an exemplary embodiment, the wafer inspecting method may further comprise displaying the discriminated defect externally by indicating the defect on a map.

In an exemplary embodiment, the inspection conditions may include a kind of light being output to scan the pattern image, a shape or amount of light being input to the unit inspection region, and a shape or amount of light being reflected in the unit inspection region.

In accordance with an exemplary embodiment, the present invention provides a wafer inspecting method comprising: scanning a pattern image of a unit inspection region in a normal state in a first mode with definite inspection conditions, and setting the scanned patterned image as a first reference image; scanning a pattern image of a unit inspection region to be inspected in the first mode, and storing the scanned pattern image as a first detection image; comparing the first reference image with the first detection image, and storing a difference between the first reference image and the first detection image as a first difference image; scanning a pattern image of a unit inspection region in a normal state in a second mode with inspection conditions that are different from the first mode, and setting the scanned pattern image as a second reference image; scanning a pattern image of a unit inspection region to be inspected in the second mode, and storing the scanned pattern image as a second detection image; comparing the second reference image with the second detection image, and storing a difference between the second reference image and the second detection image as a second difference image; generating a third difference image by calculating a balance between the first difference image and the second difference image; and discriminating a defect from noise by using the third difference image.

According to an exemplary embodiment, the discriminating of a defect from noise may comprise: calculating electrical signal values of the third difference image; and, of the calculated signal values, discriminating the signal values that exceed a predetermined threshold value as a defect and the signal values that are less than the threshold value as noise. In this exemplary embodiment, the electrical signal values may be gray level signal values.

In an exemplary embodiment, the wafer inspecting method may further comprise displaying the discriminated defect externally by indicating the defect on a map.

According to an exemplary embodiment, the scanning of a pattern image of the unit inspection region may comprise ouputting light from a light source; inputting the output light to the unit inspection region so that the output light is reflected in the unit inspection region; and inputting the reflected light in the unit inspection region to an image sensor, so that the reflected light is detected.

In an exemplary embodiment, the inspection conditions may include a kind of the light being output from the light source, a shape or amount of the light being input to the unit inspection region, and a shape or amount of the light being input to the image sensor.

According to an exemplary embodiment, the wafer inspecting method may further comprise changing a mode from a first mode to a second mode, and the changing of the mode may comprise changing the kind of the light being output from the light source. Furthermore, the changing of the mode may comprise changing the shape or amount of the light being input to the unit inspection region. In addition, the changing of the mode may comprise changing the shape or amount of the light being input to the image sensor.

BRIEF DESCRIPTION OF THE DRAWINGS

Exemplary embodiments of the present invention will be understood in more detail from the following description taken in conjunction with the attached drawings in which.

DETAILED DESCRIPTION OF EXEMPLARY EMBODIMENT

The present invention will now be described more fully hereinafter with reference to the accompanying drawings, in which exemplary embodiments of the present invention are shown. This invention may, however, be embodied in many different forms and should not be construed as being limited to the exemplary embodiments set forth herein. Rather, these exemplary embodiments are provided so that this disclosure will be thorough and complete, and will fully convey the scope of the invention to those skilled in the art. Like numbers refer to like elements throughout the specification.

Figure 2:
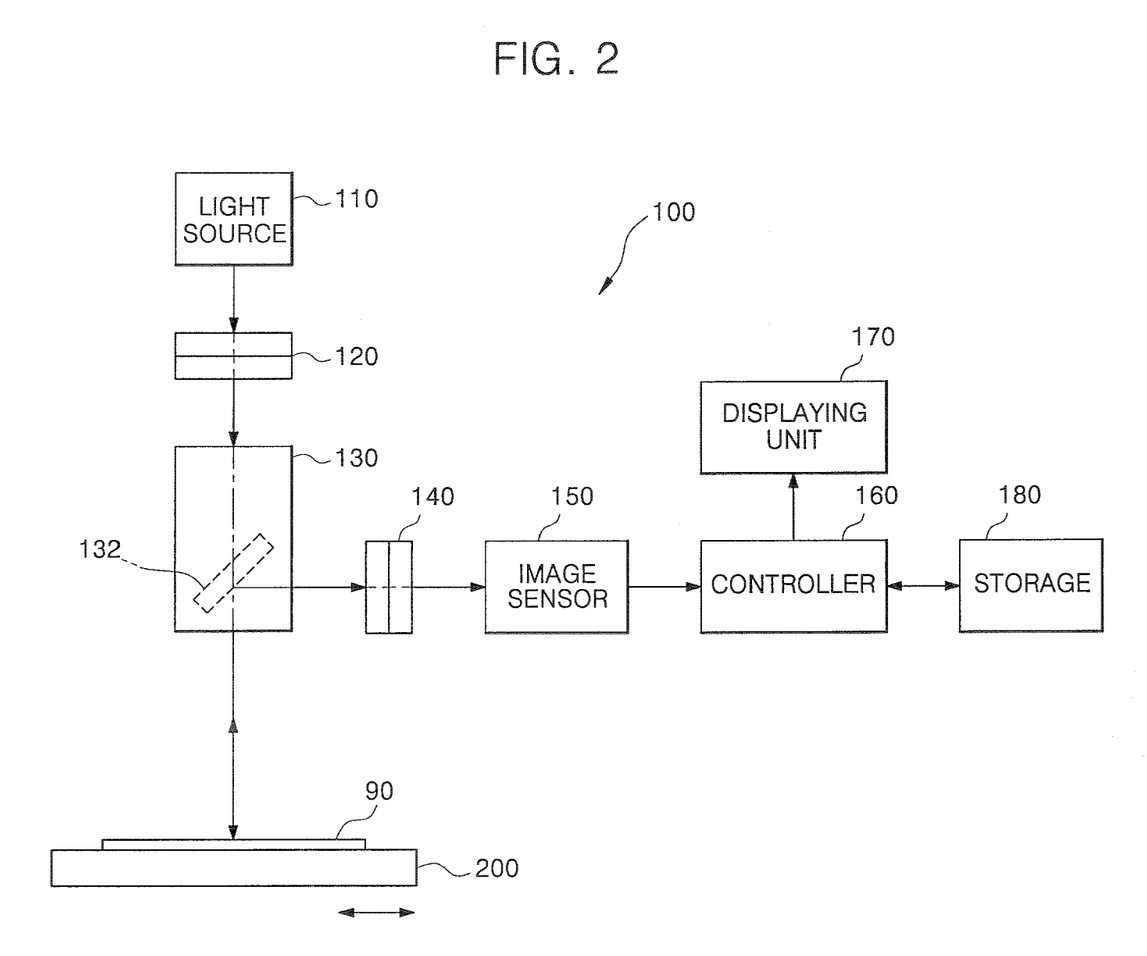
FIG. 2 is a block diagram of a wafer inspecting apparatus in accordance with an exemplary embodiment of the present invention.

FIG. 2 is a block diagram of a wafer inspecting apparatus 100 in accordance with an exemplary embodiment of the present invention.

As illustrated in FIG. 2, the wafer inspecting apparatus 100 inspects a pattern image of a wafer 90 over a predetermined unit inspection region, such as a cell or die on the wafer 90, in order to detect a defect. The wafer inspecting apparatus 100 comprises a wafer stage 200, a light source 110, an optical system 130, a first light adjusting unit 120, an image sensor 150, a second light adjusting unit 140, a storage 180, a controller 160, and a displaying unit 170.

More specifically, the wafer 90 to be inspected is held on the wafer stage 200, and the wafer stage 200 moves the wafer 90 mounted on its top surface from side to side or back and forth.

The light source 110 outputs predetermined light to be incident on the wafer 90. For example, the light source 110 outputs ultraviolet light or deep ultraviolet light.

The optical system 130 guides the light output from the light source 110 so as to be incident on the wafer 90 and guides the light being reflected from the wafer 90 so as to be received at the image sensor 150. The optical system 130 may be positioned between the light source 110 and the wafer 90 and may include a reflector 132 to reflect the light reflected from the wafer 90, to the image sensor 150. In this case, the reflector 132 may be a half mirror that transmits the light output from the light source 110 and being incident on the wafer 90 and reflects the light reflected from the wafer 90 to the image sensor 150.

The first light adjusting unit 120 is positioned between the light source 110 and the optical system 130 or within the optical system 130. The first light adjusting unit 120 changes a shape or an amount of the light that has been output from the light source 110 and that is incident on the wafer 90. As an example, the first light adjusting unit 120 changes the shape or amount of the input light so that the light from the light source 110 is all incident on the whole area of a light input region within the wafer 90 or incident to only a part, for example, an edge of the light input region within the wafer 90.

The image sensor 150 senses a pattern image of the wafer 90 by detecting the light reflected from the wafer 90. The image sensor 150 is connected to the storage 180 and the controller 160.

The second light adjusting unit 140 is positioned between the image sensor 150 and the optical system 130 or within the optical system 130. The second light adjusting unit 140 changes a shape or an amount of the light reflected from the wafer 90 and being input to the image sensor 150. As an example, the second light adjusting unit 140 changes the shape or amount of the reflected light, so that the reflected light from the wafer 90 is all incident on the whole area of a light input region within the image sensor 150 or incident to only a part, for example, an edge of the light input region within the image sensor 150.

The storage 180, connected to the controller 160 stores data from the image sensor 150 to be used for detecting a defect. As an example, a reference image used for detecting a defect is stored in the storage 180. That is, when inspecting a pattern image of the wafer 90 over the unit inspection region, the pattern image in a normal state is scanned and set as the reference image, which is then stored in the storage 180. Various difference images and threshold values of a gray level signal, which are used for detecting a defect, are also stored in the storage 180.

The controller 160 controls the wafer inspecting apparatus 100 to detect a defect. More specifically, the controller 160 generally controls the light source 110, the light adjusting units 120 and 140, and the image sensor 150, so that the pattern image of the wafer 90 is scanned in a first mode with definite inspection conditions and in a second mode with inspection conditions that are different from those of the first mode. The controller 160 compares the scanned pattern image with the reference image stored in the storage 180 and generates a difference between these images as a difference image. The controller 160 calculates a balance between one difference image generated in one mode, for example, the difference image generated in the first mode, and the other difference image generated in the other mode, for example, the difference image generated in the second mode, and generates a discrimination difference image, that is, a third difference image. The controller 160 discriminates an actual defect from noise by using the third difference image as the discrimination difference image, thereby detecting the defect. More specifically, the controller 160 calculates the gray level signal values of the third difference image which is the discrimination difference image. Of the calculated signal values, the controller 160 discriminates the signal values that exceed a predetermined threshold value stored in the storage 180 as a defect and discriminates the signal values that are less than the threshold value as noise, thereby detecting the actual defect.

The displaying unit 170 is connected to the controller 160 and displays data transmitted from the controller 160 to a user. More specifically, when the controller 160 discriminates a defect from noise and detects the defect through the above-described processes, the controller 160 transmits data of the discriminated or detected defect to the displaying unit 170. Then, the displaying unit 170 receives the transmitted defect data and indicates the discriminated or detected defect on a map, thereby displaying the defect to the user.

A wafer inspecting method, using the wafer inspecting apparatus 100, will be described, in detail, below.

Figure 3:
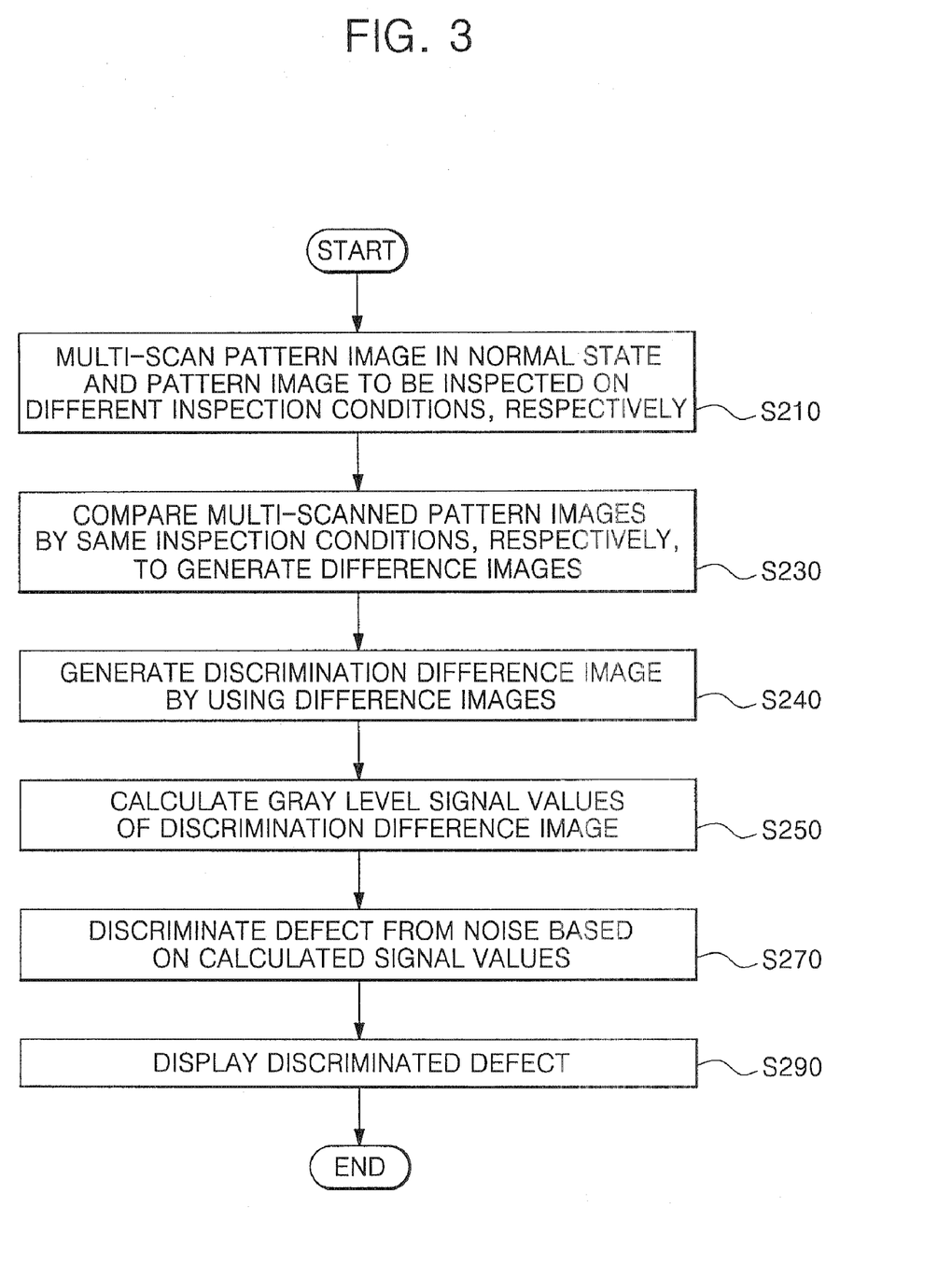
FIG. 3 is a flow chart of a wafer inspecting method in accordance with an exemplary embodiment of the present invention.

FIG. 3 is a flow chart of a wafer inspecting method in accordance with an exemplary embodiment of the present invention.

Referring to FIG. 3, in accordance with the exemplary embodiment of the wafer inspecting method, a pattern image of a unit inspection region in a normal state and a pattern image of a unit inspection region to be inspected are respectively multi-scanned under different inspection conditions (S210). As described above, the scanning of a pattern image of the unit inspection region may comprise: outputting light from the light source 110, causing the output light to be incident on the unit inspection region so that the output light is reflected by the unit inspection region, and inputting the reflected light from the unit inspection region to the image sensor 150, so that the reflected light is detected. Consequently, the image sensor 150 scans the pattern image of the unit inspection region by detecting the light reflected from the unit inspection unit. The inspection conditions may include an algorithm for comparing the pattern images, the kind of light being output from the light source to scan the pattern images, a shape or amount of the light incident on the unit inspection region, and a shape or amount of the light being reflected from the unit inspection region and being input to the image sensor. The unit inspection region may be a partial region on a wafer. For example, the unit inspection region may be a cell or die formed on the wafer.

Subsequently, the multi-scanned pattern images in the normal state are compared with the multi-scanned pattern images obtained by each of the same inspection conditions, and differences between these pattern images are respectively stored as difference images (S230).

A balance between the stored difference images is calculated, thereby generating a discrimination difference image, which is a third difference image (S240).

Therefore, when the discrimination difference image, which is the third difference image, is generated a defect is discriminated from noise by using the third difference image. The discriminating of a defect from noise may use a gray level signal value as an electrical signal value of a pattern image. That is, in the exemplary embodiment of the present invention, the discriminating of a defect from noise may comprise calculating the gray level signal values of the discrimination difference image, which is the third difference image, (S250) and of the calculated gray level signal values, discriminating the signal values that exceed a predetermined threshold value stored in the storage as a defect and the signal values that are less than the threshold value as noise (S270).

When the defect is discriminated from noise, based on the predetermined threshold value, the discriminated defect is indicated on a map which is in a wafer shape for display to the user (S290). Then, the operator watches the displayed map and very easily recognizes that a defect is present.

A wafer inspecting method in accordance with an exemplary embodiment of the present invention will be described below.

Figure 4:
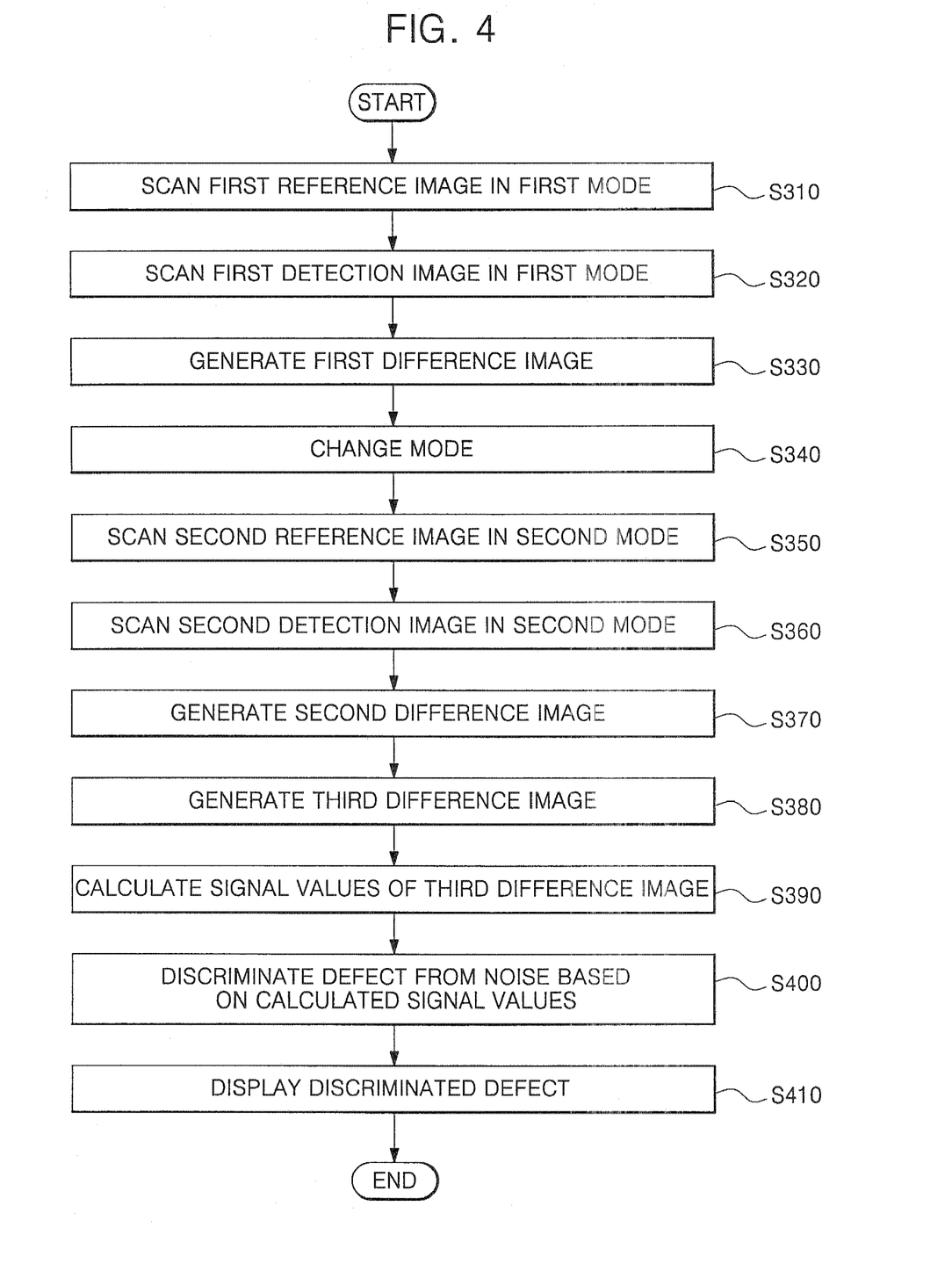
FIG. 4 is a flow chart of a wafer inspecting method in accordance with an exemplary embodiment of the present invention.

FIG. 4 is a flow chart of the wafer inspecting method in accordance with an exemplary embodiment of the present invention.

Referring to FIG. 4, a pattern image of a unit inspection region in a normal state is scanned in a first mode with definite inspection conditions and is set as a first reference image (S310). As described above, the scanning of the pattern image of the unit inspection region may comprise outputting light from the light source 110, causing the output light to be incident on the unit inspection region so that the output light is reflected from the unit inspection region, and inputting the reflected light to the image sensor 150 so that the reflected light is detected. Consequently, the image sensor 150 scans the pattern image of the unit inspection region by detecting the light reflected from the unit inspection region. The inspection conditions may include an algorithm for comparing the pattern images, the kind of light being output from the light source 110 to scan the pattern image, a shape or amount of the light incident on the unit inspection region, and a shape or amount of the light being reflected from the unit inspection region and being input to the image sensor. The unit inspection region may be a partial region on a wafer. For example, the unit inspection region may be a cell or die formed on the wafer.

Subsequently, a pattern image of the unit inspection region to be inspected is scanned in the same first mode applied when scanning the first reference image, and the scanned pattern image is stored as a first detection image (S320).

When the first reference image and the first detection image are prepared, the first reference image is compared with the first detection image, and a difference of these images is stored as a first difference image (S330). The first difference image may be a value that is a balance between the first reference image and the first detection image.

When the first difference image is prepared, the mode is changed to a second mode with different inspection conditions from the first mode (S340). The changing of the mode may comprise changing the algorithm for comparing the pattern images, changing the kind of the light being output form the light source 110, changing the shape or amount of the light incident on the unit inspection region, and changing the shape or amount of the light being input to the image sensor 150. An operator may select at least one of these changes, to change a mode.

Subsequently, when the mode is changed to the second mode, a pattern image of a unit inspection region in a normal state is scanned in the second mode, and the scanned pattern image is set as a second reference image (S350). A pattern image of a unit inspection region to be inspected is scanned in the second mode, and the scanned pattern image is stored as a second detection image (S360).

When the second reference image and the second detection image are prepared, the second reference image is compared with the second detection image, and a difference of these images is stored as a second difference image (S370). The second difference image may be a vale that is a balance between the second reference image and the second detection image.

When the first difference image and the second difference image that are respectively generated through the different modes are prepared, a balance between the first difference image and the second difference image is calculated, thereby generating a third difference image (S380).

After the third difference image is generated, a defect is discriminated from noise by using the third difference image. The discriminating of a defect from noise may use a gray level signal value that is an electrical signal value of a pattern image. That is, in the exemplary embodiment of the present invention, the discriminating of a defect from noise may comprise calculating the gray level signal values of the third difference image (S390) and, of the calculated gray level signal values, discriminating the signal values that exceed a predetermined threshold value stored in the storage 180 as a defect and the signal values that are less than the threshold value as noise (S400).

Subsequently, when the defect is discriminated from the noise, based on the predetermined threshold value, the discriminated defect is indicated on a map that is in a wafer shape, to be displayed (S410) to the operator. Then, the operator watches the externally displayed map and very easily recognizes that a defect is present.

Figure 5:
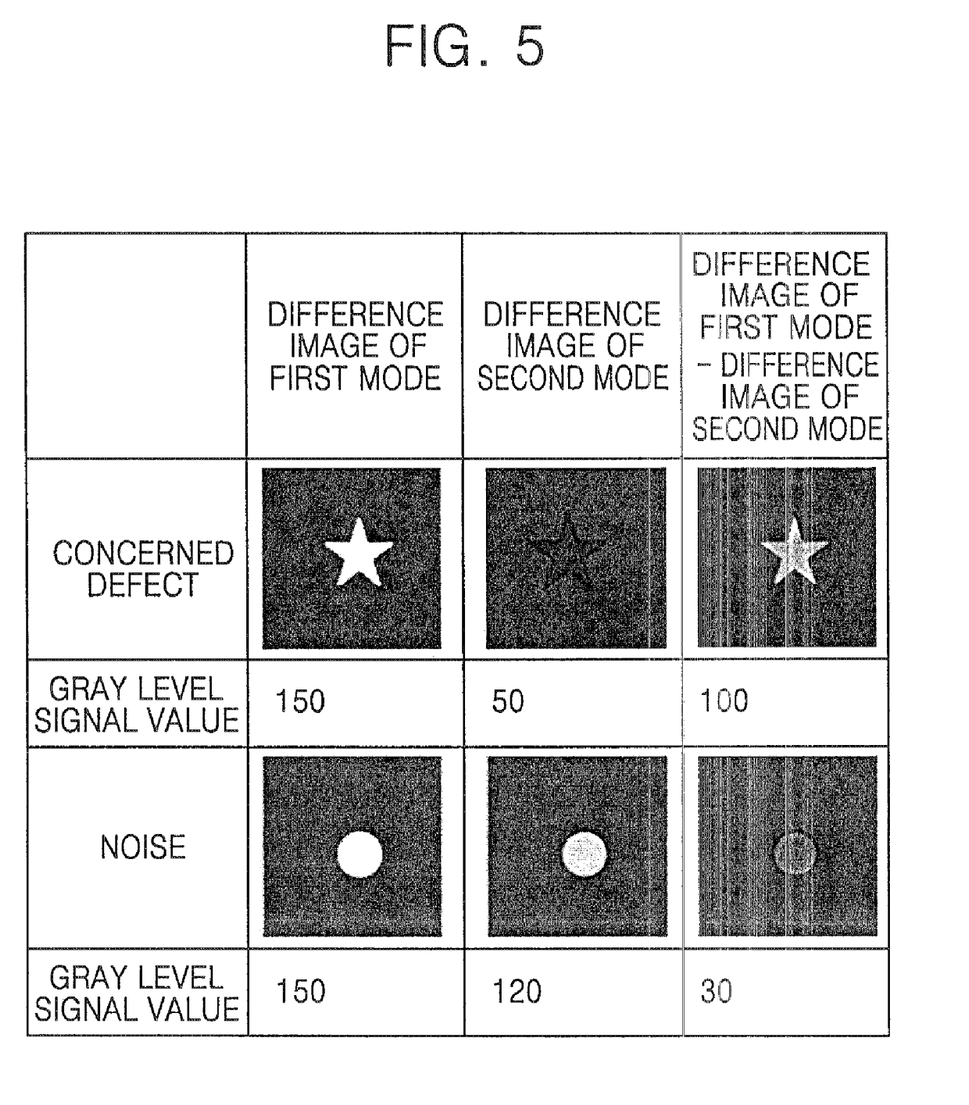
FIG. 5 provides images useful in explaining a wafer inspecting method in accordance with an exemplary embodiment of the present invention.

FIG. 5 provides images useful in explaining a wafer inspecting method in accordance with an exemplary embodiment of the present invention.

The wafer inspecting method will be described, in more detail, with reference to FIG. 5 below.

As illustrated in FIG. 5, when a defect and noise co-exist in a specific unit inspection region and their signal values are similar to each other, the defect cannot be easily discriminated from the noise by the conventional wafer inspecting method. When using the wafer inspecting method in accordance an exemplary embodiment of the present invention, however, the defect is easily discriminated from the noise.

That is, when a defect exists with noise in a specific unit inspection region of a wafer, an operator scans a pattern image of the unit inspection region in the normal state and a pattern image of the specific unit inspection region including both concerned defect and noise, in any one mode, for example, the first mode, with the inspection conditions that the signal value of a defect and the signal value of noise are both large. Then, the operator calculates a difference of these pattern images, to generate a first mode difference image shown in FIG. 5. When the gray level signal values of the concerned defect and noise are calculated in the first mode difference image, the gray level signal value of the concerned defect and the gray level signal value of the noise are respectively indicated as 150.

Subsequently, the operator scans a pattern image of the unit inspection region in the normal state and a pattern image of he specific unit inspection region where the concerned defect and the noise co-exist, in another mode, for example, the second mode, on the inspection conditions that the signal value of the defect is small but the signal value of the noise is large. Then, the operator calculates a difference of these pattern images, to generate a second mode difference image. When the gray level signal values of the concerned defect and noise are calculated in the second mode difference image, the gray level signal value of the concerned defect is indicated as 60 and the gray level signal value of the noise is indicated as 120.

The operator then calculates a balance between the first mode difference image and the second mode difference image, to generate a discrimination difference image, which is the third difference image shown in FIG. 5. When the gray level signal values of the concerned defect and noise are calculated in the discrimination difference image, the gray level signal value of the concerned defect is indicated as 100 and the gray level signal value of the noise is indicated as 30.

Accordingly, when the threshold value of the gray level signal value is set at about 70 in the discrimination difference image, which is the third difference image, and the signal value more than 70 is set to be discriminated as a defect, the defect is very easily discriminated from the noise, and only the defect is detected.

As described above, the wafer inspecting method in accordance with exemplary embodiment of he present invention is performed by multi-scanning the reference image and the detection image on the difference inspection conditions, respectively; comparing the multi-scanned images by each of the same inspection conditions, to generate difference images; generating the discrimination difference image, which is the third difference image, by using the generated difference images; and inspecting the wafer based on the gray level signal values of the generated discrimination difference image. Thus, a defect is very easily discriminated from noise, and the defect is very easily detected.

The present invention has been described in reference to the exemplary embodiments illustrated in the drawings. It is to be understood, however, that the scope of the invention is not limited to the disclosed exemplary embodiments. On the contrary, the scope of the invention is intended to include various modifications and alternative arrangements within the capabilities of persons skilled in the art using presently known or future technologies and equivalents. The scope of the claims, therefore, should be accorded the broadest interpretation so as to encompass all such modifications and similar arrangements.

What is claimed is:

1. A wafer inspecting method comprising:
    scanning a pattern image of a unit inspection region of a first wafer in a normal state in a first mode with definite inspection conditions, and setting the scanned pattern image as a first reference image;
    scanning a pattern image of a unit inspection region of a second wafer to be inspected in the first mode, and storing the scanned pattern image as a first detection image;
    comparing the first reference image and the first detection image, and storing a difference of the images as a first difference image;
    scanning a pattern image of the unit inspection region of the first wafer in the normal state in a second mode with inspection conditions different from the first mode, and setting the scanned pattern image as a second reference image;
    scanning a pattern image of the unit inspection region of the second wafer to be inspected in the second mode, and storing the scanned pattern image as a second detection image;
    comparing the second reference image and the second detection image, and storing a difference of the images as a second difference image;
    generating a third difference image by calculating a balance between the first difference image and the second difference image; and
    discriminating a defect from noise by using the third difference image.

2. The method according to claim 1, wherein the step of discriminating a defect from noise comprises:
    calculating electrical signal values of the third difference image; and of the calculated signal values, discriminating the signal values that exceed a predetermined threshold value as a defect and the signal values that are less than the threshold value as noise.

3. The method according to claim 2, wherein the electrical signal values are gray level signal values.

4. The method according to claim 1, further comprising: displaying the discriminated defect externally on a map.

5. The method according to claim 1, wherein the step of scanning the pattern image of the unit inspection region comprises:
outputting light from a light source;
inputting the output light to the unit inspection region so that the output light is reflected from the unit inspection region; and
inputting the reflected light from the unit inspection region to an image sensor so that the reflected light is detected.

6. The method according to claim 5, wherein the inspection conditions include a kind of light used to scan the pattern image, a shape or amount of light being input to the unit inspection region, and a shape or amount of light being reflected from the unit inspection region.

7. The method according to claim 5, further comprising: changing a mode from the first mode to the second mode.

8. The method according to claim 7, wherein the changing of a mode comprises changing the kind of the light being output from the light source.

9. The method according to claim 7, wherein the changing of a mode comprises changing the shape or amount of the light being input to the unit inspection region.

10. The method according to claim 7, wherein the changing of a mode comprises changing the shape or amount of the light being input to the image sensor.

11. The method according to claim 1, wherein the unit inspection region is an entire wafer being inspected.

12. The method according to claim 1, wherein the unit inspection region is a cell or die portion on a wafer being inspected.

* * * * *